United States Patent
Cui et al.

(10) Patent No.: US 6,380,375 B1
(45) Date of Patent: Apr. 30, 2002

(54) DNA ENCODING MONKEY GONADOTROPIN RELEASING HORMONE RECEPTOR

(75) Inventors: Jisong Cui, Scotch Plains; Jane-Ling Lo, North Brunswick, both of NJ (US); George R. Mount, Morrisville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/501,192

(22) Filed: Feb. 10, 2000

Related U.S. Application Data

(60) Provisional application No. 60/121,780, filed on Feb. 26, 1999, and provisional application No. 60/138,135, filed on Jun. 8, 1999.

(51) Int. Cl.⁷ .......................... C12N 5/10; C12N 15/12; C12N 15/63; C12N 15/64; C07K 14/72
(52) U.S. Cl. .................... 536/23.5; 435/71.1; 435/71.2; 435/471; 435/325; 435/252.3; 435/254.11; 435/320.1; 435/69.1
(58) Field of Search .......................... 530/350; 536/23.1, 536/23.5; 435/69.1, 71.1, 71.2, 471, 325, 252.3, 254.11, 320.1

(56) References Cited

U.S. PATENT DOCUMENTS

| | | |
|---|---|---|
| 5,750,366 A | 5/1998 | Sealfon |
| 5,985,583 A | 11/1999 | Sealfon |

OTHER PUBLICATIONS

Molecular Endocrinology, vol. 4, pp. 119–124 (1990), by Sealfon, et al.
Molecular Endocrinology, vol. 6, No. 7, pp. 1163–1169 (1992), by Tsutsumi, et al.
Molecular & Cellular Endocrinology, vol. 90, pp. R5–R9 (1992), by Eidne, et al.
Biochmical & Biophysical Research Communications, vol. 189, No. 1, pp. 289–295 (1992), by Kakar, et al.
Molecular & Cellular Endocrinology, vol. 91, pp. R1–R6 (1993), by Chi, et al.
Fraser, et al., Mol. Human Reprod., vol. 2, No. 2, pp. 117–121, 1996.
Sambrook, et al., Molecular Cloning,vol. 3, pp. 17.2–17.11 and 17.42–17.44, 1989.

*Primary Examiner*—Prema Mertz
(74) *Attorney, Agent, or Firm*—Valerie J. Camara; Mark R. Daniel

(57) ABSTRACT

The monkey GnRH receptor has been isolated, cloned and sequenced. The monkey GnRH receptor may be used to screen and identify compounds which bind to the GnRH receptor. Such identified compounds may be used in the treatment of sex hormone related conditions such as endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertrophy. The receptor proteins and polypeptides, nucleic acids, cells and assays of this invention are useful in drug screening and development, diagnosis and therapeutic applications.

6 Claims, 9 Drawing Sheets

Human 1; 5'-ATGCGAATTCGCCACCATGGCAAACAGTGCCTCTCC-3' (SEQ ID No. 1)
Human 3; 5'-ATGCTCTAGATCACAGAGAAAAATATCC ATAGATAAGTGG-3'(SEQ ID No. 2)
Monkey 1; 5'-ACTTCAGAAGTGGACACAG-3' (SEQ ID No. 3)
Monkey 2; 5'-CAGAGGAACTCTCCAGCATAC-3' (SEQ ID No. 4)
Monkey 5; 5'-ATATCCATAGATAAGTGGATC-3' (SEQ ID No. 5)
HRE 3; 5'-TCCATAGATAAGTGGATCAAAGC-3' (SEQ ID No. 6)
Monkey 6; 5'-CATTCACTGTCTGCTGGAC-3' (SEQ ID No. 7)

Figure 1

```
atggcaaacagtgcctcacctgaacagaatcaaaatcactgttcagtcatcaacaacagc
atcccactgatgcagggcaacctccccactctgaccttgtctggaaagatccgagtgaca
gttactttcttccttttctactctctgcgacctttaatgcttctttcctgctgaaactt
cagaagtggacacagaagaaagagaaagggaaaaagctgtcaagaatgaagctgctctta
aaacatctgaccttagccaacctgttggagactctgattgtcatgccactggatgggatg
tggaacattacagtccaatggtatgctggagagttcctctgcaaagttctcagttatcta
aagcttttctccatgtatgccccagctttcatgatggtggtgatcagcctggaccgctcc
ctggctatcacgaggcccctagctttgaaaagcagcagcaagctcggacagtccatggtt
ggcctggcctggatcctcagtagtgtctttgcaggaccacagttatacatcttcaggatg
attcatctagcagacagctccggacagacaaaagtttctctcaatgtgtaacacactgc
agttttccacaatggtggcatcaagcatttataacttttcaccttcagctgcctcttc
atcatcctcttctcatcatgctgatctgcaatgcaaaaatcatcttcaccctgacacgg
gtccttcatcaggatccccacaaactacaactgaatcagtccaagaacaatataccaaga
gcacggctgaagactctaaaaatgacagttgcatttgccacttcattcactgtctgctgg
actccctactatgtcctaggaatttggtattggtttgatcctgaaatgttaaacagggtg
tcagacccagtaaatcacttcttctttctctttgccttttaaacccatgctttgatcca
cttatctatggatattttctctgtga
```

Figure 2

MANSASPEQNQNHCSVINNSIPLMQGNLPTLTLSGKIRVTVTFFLFLLSATFNASFLLKL

QKWTQKKEKGKKLSRMKLLLKHLTLANLLETLIVMPLDGMWNITVQWYAGEFLCKVLSYL

KLFSMYAPAFMMVVISLDRSLAITRPLALKSSSKLGQSMVGLAWILSSVFAGPQLYIFRM

IHLADSSGQTKVFSQCVTHCSFPQWWHQAFYNFFTFSCLFIIPLLIMLICNAKIIFTLTR

VLHQDPHKLQLNQSKNNIPRARLKTLKMTVAFATSFTVCWTPYYVLGIWYWFDPEMLNRV

SDPVNHFFFLFAFLNPCFDPLIYGYFSL*

Figure 3

```
acatgtggccctcagaatgcgtttggcctgctctgttttagccctctgttggattaccaa
tacacaaaacaagttaaccttgatctttctcattaagtatctcagggacaaaatttgaca
tacgtctaaacctgtgacgtttccatctaaagaaggcagaaataaaacaggactttagat
tcggttacaataaaatatcagatgcgccacagacacaagtcttgaagctctgtcctggga
aaat
```

Figure 4

DNA ENCODING MONKEY GONADOTROPIN RELEASING HORMONE RECEPTOR

This application claims the benefit of U.S. Provisional Application Nos. 60/121,780, filed Feb. 26, 1999 and 60/138,135, filed Jun. 8, 1999.

FIELD OF THE INVENTION

This invention relates to the cloning and isolation of the monkey gonadotropin-releasing hormone (GnRH) receptor, and also to mutant or polymorphic forms of the receptor and recombinant nucleic acids encoding the same. The invention also relates to genetically engineered host cells which express the receptor, antibodies against the receptor and polypeptides thereof. The invention also relates to uses of the receptor, recombinant nucleic acids and recombinant host cells in drug screening and development, diagnosis and therapeutic applications.

BACKGROUND OF THE INVENTION

Gonadotropin-releasing hormone (GnRH) plays a pivotal role in the control of reproduction. It is a neuronal decapeptide hormone released from hypothalamus in a pulsatile manner. GnRH interacts with its receptor on the gonadotropes in the anterior pituitary and which, in turn, activates phospholipase C (PLC) via a pertussis toxin-insensitive G protein, Gq/G11. Two second messengers, inositol trisphosphate (IP3) and diacylglycerol (DG), are formed from the hydrolysis of phosphoinositide bisphosphate by PLC. IP3 and DG then act either separately or in concert, via increase of intracellular $Ca^{2+}$ and activation of protein kinase C, to regulate the synthesis and release of both luteinizing hormone (LH) and follicle stimulating hormone (FSH). LH released from the pituitary gland is primarily responsible for the regulation of gonadal steroid production in both sexes, whereas FSH regulates spermatogenesis in males and follicle development in females.

The GnRH receptor (GnRH-R) is mainly expressed in the pituitary gland. It was also detected in extrapituitary tissues such as brain, breast, gonads, and ovarian tumors. The GnRH receptor has been cloned and sequenced from several mammalian species including human, ovine, bovine, pig, rat, and mouse. The cloning and expression of the murine and human receptors has recently been described in U.S. Pat. No. 5,750,366. The GnRH receptor from bovine, cow, sheep, and human contains 328 amino acids, while the rodent receptor has 327 amino acids, due to a deletion of a residue in the second extracellular domain. Analysis of the primary sequence identifies the GnRH receptor as a member of the G protein-coupled receptor (GPCR) family with seven transmembrane (TM) domains. However, the mammalian GnRH receptors have several unique structural features compared with other GPCRs. These include (1) the lack of the entire intracellular C-terminal tail; (2) the replacement of Tyr by Ser in the conserved G protein signature DRY motif of the proximal second intracellular domain; and (3) the reciprocal exchange of two amino acids, Asp in TM II and Asn in TM VII, that are highly conserved in most other GPCRs. In addition to pituitary gland, the expression of GnRH receptor message has also been demonstrated in extrapituitary tissues such as brain, breast, gonads, and ovarian tumors. The receptor sequences obtained from extrapituitary sources were identical to the corresponding pituitary GnRH receptor cDNAs.

Synthetic peptidyl GnRH analogues have been widely used in treating patients with prostate and breast cancers, endometriosis, uterine fibroids, precocious puberty, and other endocrinological disorders. Continuous infusion of high dose GnRH agonists internalizes the GnRH receptor and subsequently desensitizes the receptor, therefore effectively reducing the levels of LH and FSH. However, GnRH agonists can cause flare of the disease at the initial use due to their stimulatory effects. Cetrorelix and other peptide antagonists which are under development have been shown to reduce the levels of LH and FSH without the flare effect. Non-peptidyl GnRH antagonists have been disclosed in U.S. Pat. Nos. 5,756,507, 5,780,437 and 5,849,764.

Although the monkey has been used to evaluate the efficacy of GnRH agonists and antagonists in vivo, its GnRH receptor has not been cloned and expressed in any cell lines. Without the intrinsic potency of the test compound, it is difficult to interpret in vivo results. In this invention, we have cloned and sequenced the monkey GnRH receptor and functionally expressed the receptor in a mammalian cell system. These tools facilitate the development of better GnRH agonists or antagonists for treating some reproductive disorders.

SUMMARY OF THE INVENTION

This invention relates to the cloning and sequencing of the monkey GnRH receptor. The DNA sequences disclosed herein may be engineered into expression systems designed for the production of the receptor and/or cell lines which express the receptor. Such cell lines may be used for screening and identifying compounds that function as GnRH agonists and antagonists.

Another aspect of this invention are nucleic acids which encode the receptor or a functional equivalent. These nucleic acids may be free from associated nucleic acids, or they may be isolated or purified. For most cloning purposes, cDNA is a preferred nucleic acid, but this invention specifically includes other forms of DNA as well as RNAs which encode the receptor or a functional equivalent.

A further aspect of this invention relates to vectors which comprise nucleic acids encoding the monkey GnRH receptor or a functional equivalent. These vectors may be comprised of DNA or RNA; however, for most cloning purposes, DNA vectors are preferred. Typical vectors include plasmids, modified viruses, bacteriophage and cosmids, yeast artificial chromosomes and other forms of episomal or integrated DNA that can encode the receptor. It is well within the skill of the ordinary artisan to determine an appropriate vector for a particular gene transfer or other use.

Another aspect of this invention are host cells which are transformed with a gene which encodes the monkey GnRH receptor or a functional equivalent. The host cell may or may not naturally express the receptor on the cell membrane. Preferably, once transformed, the host cells are able to express the receptor or a functional equivalent on the cell membrane. Depending on the host cell, it may be desirable to adapt the DNA so that particular codons are used in order to optimize expression. Such adaptations are known in the art, and these nucleic acids are also included within the scope of this invention. Generally, mammalian cell lines, such as COS, HEK-293, CHO, HeLa, NS/O, CV-1, GC, GH3 or VERO cells are preferred host cells, but other cells and cell lines such as Xenopus oocytes or insect cells, may also be used.

A final aspect of this invention are assays to detect agonists and antagonists of the receptor. In particular, cells comprising the monkey GnRH receptor are used in screening assays such as binding assays using the cell membrane or the whole cell and functional assays such as the phosploinositide turnover (PI) and the $Ca^{2+}$ release. All of these assays are well known and simply adapted by one of skill in the art.

BRIEF DESCRIPTION OF THE FIGURES

FIG. 1 shows the primers used in the invention, as set forth in SEQ ID Nos. 1–7.

FIG. 2 is the DNA of the monkey GnRH receptor that encodes the entire open reading frame, from Met Initiation codon to the Stop codon, as set forth in SEQ ID No. 8.

FIG. 3 is the amino acid sequence of the monkey GnRH receptor encoded by the DNA in FIG. 2, as set forth in SEQ ID No. 9.

FIG. 4 is the partial DNA sequence of the monkey GnRH receptor contained in exon 1, located immediately upstream of the Start codon ATG, as set forth in SEQ ID No. 10.

DETAILED DESCRIPTION OF THE INVENTION

Figure 5:
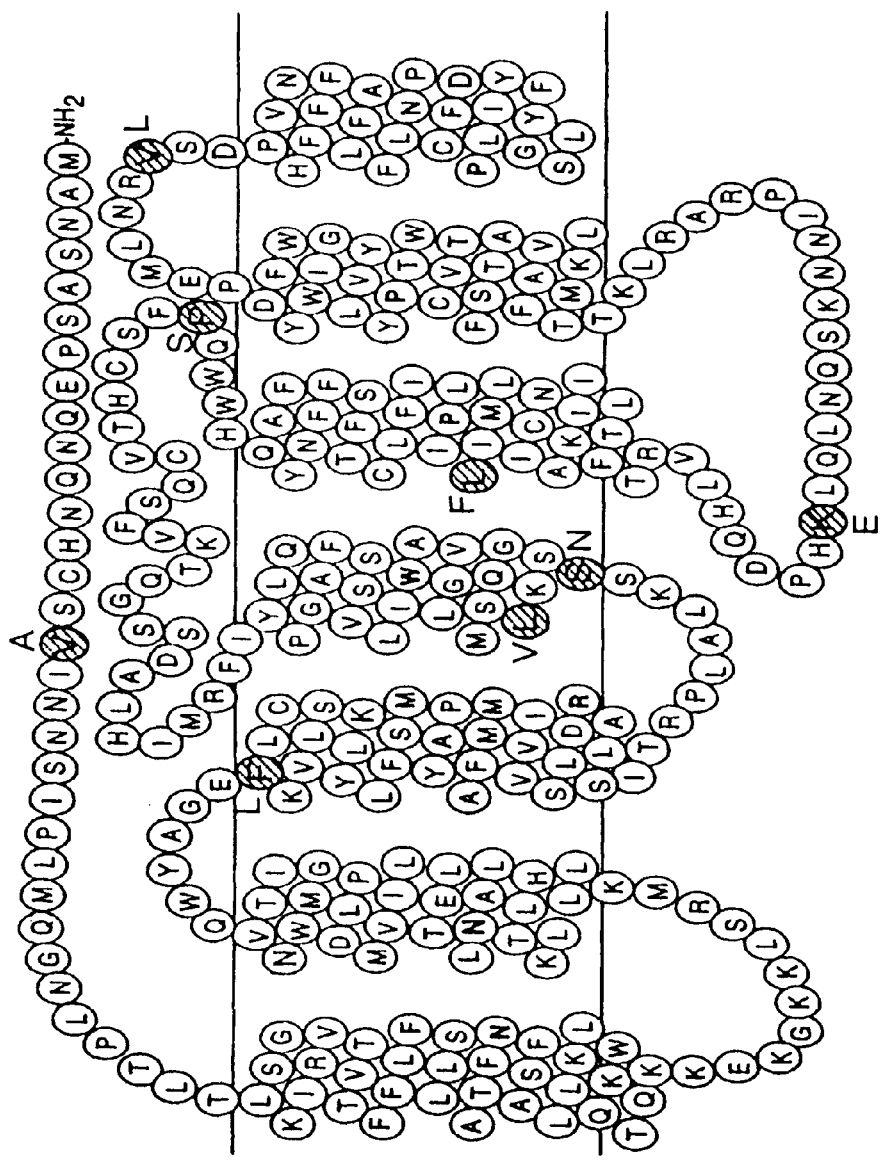
FIG. 5 shows the amino acid sequence of the monkey GnRH receptor in its proposed configuration in the plasma membrane. The residues that differ from the human receptor were shaded and compared (the human residues are outside the circle).

This invention relates to the cloning of the monkey gonadotropin-releasing hormone (GnRH) receptor, and also to mutant or polymorphic forms of the receptor and recombinant nucleic acids encoding the same. The invention also relates to genetically engineered host cells which express the receptor as well as antibodies against the receptor and polypeptides thereof The invention also relates to uses of the receptor, recombinant nucleic acids and recombinant host cells in drug screening and development, diagnosis and therapeutic applications.

Each document mentioned in this specification is hereby incorporated herein by reference in its entirety.

As used herein a "compound" or a "molecule" is an organic or inorganic assembly of atoms of any size, and can include macromolecules, e.g., peptides, polypeptides, whole proteins, and polynucleotides. The terms are used interchangeable herein.

As used herein, a "candidate" is a molecule or compound that may be a modulator, agonist or antagonist of the receptor.

As used herein an "agonist" is a compound or molecule that interacts with and activates a polypeptide of the receptor.

As used herein an "antagonist" is a compound or molecule that interacts with and inhibits or prevents a polypeptide of the receptor from becoming activated.

As used herein a "modulator" is a compound or molecule that interacts with an aspect of cellular biochemistry to effect an increase or decrease in the amount of a polypeptide of the receptor present at the surface of a cell, or in the surrounding serum or media. The change in amount of the receptor polypeptide can be mediated by the effect of a modulator on the expression of the receptor, e.g., the transcription, translation, post-translational processing, translocation or folding of the receptor, or by affecting a component(s) of cellular biochemistry that directly or indirectly participates in the expression of the receptor. Alternatively, a modulator can act by accelerating or decelerating the turnover of the receptor either by direct interaction with the receptor or by interacting with another component(s) of cellular biochemistry which directly or indirectly effects the change.

As used herein a "polynucleotide" is a nucleic acid of more than one nucleotide. A polynucleotide can be made up of multiple poly-nucleotide units that are referred to by description of the unit. For example, a polynucleotide can comprise within its bounds a polynucleo-tide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the vector can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

The isolated nucleic acid molecule of the present invention can include a deoxyribonucleic acid molecule (DNA), such as genomic DNA and complementary DNA (cDNA), which can be single (coding or noncoding strand) or double stranded, as well as synthetic DNA, such as a synthesized, single stranded polynucleotide. The isolated nucleic acid molecule of the present invention can also include a ribonucleic acid molecule (RNA).

The present invention also relates to recombinant vectors and recombinant hosts, both prokaryotic and eukaryotic, which contain the substantially purified nucleic acid molecules disclosed throughout this specification.

Polynucleotides of this invention contain full length or partial length sequences of the receptor gene. Polynucleotides of this invention can be single or double stranded. If single stranded, the polynucleotides can be a coding, "sense," strand or a complementary, "antisense," strand. Antisense strands can be useful as modulators of the receptor by interacting with RNA encoding the receptor. Antisense strands are preferably less than full length strands having sequences unique or highly specific for RNA encoding the receptor.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methyl-cytosine, deazaguanosine, etc., can be present. Natural phosphodiester internucleotide linkages can be appropriate. However, polynucleotides can have non-natural linkages between the nucleotides. Non-natural linkages are well known in the art and include, without limitation, methylphosphonates, phosphorothioates, phosphorodithionates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxyethyl, methacrylamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotides, proteins and polypeptides, or respective fragments thereof in question has been removed from its in vivo environment so that it can be manipulated by the skilled artisan, such as but not limited to sequencing, restriction digestion, site-directed mutagenesis, and subcloning into expression vectors for a nucleic acid fragment as well as obtaining the protein or protein fragment in pure quantities so as to afford the opportunity to generate polyclonal antibodies, monoclonal antibodies, amino acid sequencing, and peptide digestion. Therefore, the nucleic acids claimed herein can be present in whole cells or in cell lysates or in a partially purified or substantially purified form. A polynucleotide is considered purified when it is purified away from environmental contaminants. Thus, a polynucleotide isolated from cells is considered to be substantially purified when purified from cellular components by standard methods while a chemically synthesized nucleic acid sequence is considered to be substantially purified when purified from its chemical precursors.

It is known that there is a substantial amount of redundancy in the various codons which code for specific amino acids. Therefore, this invention is also directed to those DNA sequences encode RNA comprising alternative codons which code for the eventual translation of the identical amino acid, as shown below:

A=Ala=Alanine: codons GCA, GCC, GCG, GCU

C=Cys=Cysteine: codons UGC, UGU

D=Asp=Aspartic acid: codons GAC, GAU

E=Glu=Glutamic acid: codons GAA, GAG

F=Phe=Phenylalanine: codons UUC, UUU

G=Gly=Glycine: codons GGA, GGC, GGG, GGU

H=His=Histidine: codons CAC, CAU

I=Ile=Isoleucine: codons AUA, AUC, AUU

K=Lys=Lysine: codons AAA, AAG

L=Leu=Leucine: codons UUA, UUG, CUA, CUC, CUG, CUU

M=Met=Methionine: codon AUG

N=Asp=Asparagine: codons AAC, AAU

P=Pro=Proline: codons CCA, CCC, CCG, CCU

Q=Gln=Glutamine: codons CAA, CAG

R=Arg=Arginine: codons AGA, AGG, CGA, CGC, CGG, CGU

S=Ser=Serine: codons AGC, AGU, UCA, UCC, UCG, UCU

T=Thr=Threonine: codons ACA, ACC, ACG, ACU

V=Val=Valine: codons GUA, GUC, GUG, GUU

W=Trp=Tryptophan: codon UGG

Y=Tyr=Tyrosine: codons UAC, UAU

Therefore, the present invention discloses codon redundancy which can result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

As used herein, a "biologically active equivalent" or "functional derivative" of a wild-type monkey GnRH receptor possesses a biological activity that is substantially similar to the biological activity of the wild type monkey receptor. The term "functional derivative" is intended to include the "fragments," "mutants," "variants," "degenerate variants," "analogs" and "homologues" or to "chemical derivatives" of the wild type monkey receptor. The term "fragment" is meant to refer to any polypeptide subset of wild-type monkey receptor. The term "mutant" is meant to refer to a molecule that may be substantially similar to the wild type form but possesses distinguishing biological characteristics. Such altered characteristics include but are in no way limited to altered substrate binding, altered substrate affinity and altered sensitivity to chemical compounds affecting biological activity of the monkey receptor or monkey receptor functional derivative. The term "variant" is meant to refer to a molecule substantially similar in structure and function to either the entire wild-type protein or to a fragment thereof. A molecule is "substantially similar" to a wild-type monkey receptor if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the full-length monkey receptor or to a biologically active fragment thereof.

A protein or fragment thereof is considered purified or isolated when it is obtained at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature.

Probes can be labeled by any number of ways known in the art including isotopes, enzymes, substrates, chemiluminescent, electro-chemiluminescent, biotin and fret pairs among many others. A probe so labeled can generate a detectable signal directly (e.g., isotopes), or upon hybridization (fret pairs), or indirectly after a chemical (e.g., luminescence) or biochemical reaction (e.g., enzymesubstrate) or after binding a strepavidin linked moiety that can generate a detectable signal directly or indirectly. The labeling of probes and the generation of detectable signals are well known techniques in the art and include Polymerase Chain Reaction and Reverse Transcriptase Polymerase Chain Reaction (See e.g., PCR Primer, edited by C. W. Dieffenbach and G. S. Dveksler, (1995). Cold Spring Harbor Laboratory Press.), Strand Displacement Amplification, Self-Sustained Sequence Reaction, and any other amplification known to one of skill in the art that uses primers.

Expression of the Receptor

The present invention also relates to recombinant vectors and recombinant hosts, both prokaryotic and eukaryotic, which contain the substantially purified nucleic acid molecules disclosed throughout this specification.

Therefore, the present invention also relates to methods of expressing the monkey GnRH receptor and biological equivalents disclosed herein, assays employing these recombinantly expressed gene products, cells expressing these gene products, and modulators, agonistic and/or antagonistic compounds identified through the use of assays utilizing these recombinant forms, including, but not limited to, one or more compounds or molecules that act through direct contact with the receptor, particularly with the ligand binding domain, or through direct or indirect contact with a ligand which either interacts with the receptor or with the transcription or translation of GnRH, thereby modulating GnRH expression.

A variety of expression vectors can be used to express the monkey GnRH receptor in host cells. Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors can include, but are not limited to, cloning vectors, modified cloning vectors, specifically designed plasmids or viruses.

Commercially available mammalian expression vectors which can be suitable for the monkey GnRH receptor expression, include but are not limited to, pcDNA3.1 (Invitrogen), pIRES1neo (Clontech), pLITMUS28, pLITMUS29, pLITMUS38 and pLITMUS39 (New England Biolabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors can be used to express the monkey GnRH receptor in bacterial cells. Commercially available bacterial expression vectors which are suitable for recombinant monkey GnRH receptor expression include, but are not limited to pQE (Qiagen), pET11a (Novagen), lambda gt11 (Invitrogen), and pKK223-3 (Pharmacia).

A variety of fungal cell expression vectors can be used to express the monkey GnRH receptor in fungal cells. Commercially available fungal cell expression vectors which are suitable for the monkey GnRH receptor expression include but are not limited to pYES2 (Invitrogen) and Pichia expression vector (Invitrogen).

A variety of insect cell expression vectors can be used to express recombinant receptor in insect cells. Commercially available insect cell expression vectors which are suitable for the monkey GnRH receptor include but are not limited to pBlueBacIII and pBlueBacHis2 (Invitrogen), and pAcG2T (Pharmingen).

An expression vector containing DNA encoding the monkey GnRH receptor can be used for expression of the monkey GnRH receptor in a recombinant host cell. Recombinant host cells can be prokaryotic or eukaryotic, including but not limited to bacteria such as $E.\ coli$, fungal cells such as yeast, mammalian cells including but not limited to cell lines of human, bovine, porcine, monkey and rodent origin, and insect cells including but not limited to Drosophila- and silkworm-derived cell lines. Cell lines derived from mammalian species which can be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

The expression vector can be introduced into host cells via any one of a number of techniques including but not limited to transformation, transfection, protoplast fusion, and electroporation. The expression vector-containing cells are individually analyzed to determine whether they produce the monkey GnRH receptor. Identification of the monkey GnRH receptor expressing cells can be done by several means, including but not limited to immunological reactivity with anti-monkey GnRH antibodies, labeled ligand binding and the presence of host cell associated GnRH activity.

The cloned monkey GnRH receptor cDNA obtained through the methods described herein can be recombinantly expressed by molecular cloning into an expression vector (such as pcDNA3.1, pIRES1neo, pQE, pBlueBacHis2 and pLITMUS28) containing a suitable promoter and other appropriate transcription regulatory elements, and transferred into prokaryotic or eukaryotic host cells to produce recombinant human HG38. Techniques for such manipulations can be found described in Sambrook, et al., supra, and are well known and easily available to the one of ordinary skill in the art.

EXAMPLE 1 mRNA Isolation and cDNA Synthesis

Total RNA from monkey pituitaries (snap-frozen in liquid nitrogen within 1–2 minutes of animal sacrifice, California Regional Primate Research Center, Davis, Calif.) was prepared using the TRIzol reagents (Promega, Madison, Wiss.) following the manufacturer's instruction. Typically, 0.5 mg of total RNA was isolated from 350 mg wet weight of pituitary tissue. Poly (A) RNA was isolated from total RNA by column chromatography on oligo (dT) cellulose (Promega, Madison, Wis.). The yield of poly (A) mRNA from total RNA was usually 0.5%.

First-strand cDNA was synthesized from poly (A)$^+$ mRNA using SuperScript II reverse transcriptase (GIBCO-BRL, Grand Island, NY) as per the manufacture's instruction. One-tenth of the volume was used for each RT-PCR reaction.

EXAMPLE 2

Cloning and Seguencing of the Monkey GnRH Receptor cDNA

The entire open reading frame (ORF) of the monkey GnRH receptor cDNA was cloned from monkey pituitary mRNA by RT-PCR using primers Human 1 (5')+Human 3 (3') (SEQ ID Nos. 1 and 2). These primers were designed according to the DNA sequence of the human GnRH receptor. The PCR was performed using PCR kit (GIBCO-BRL, Grand Island, NY), and using the condition of 94° C. for 80 seconds, 60° C. for 1 minute, and 72° C. for 2 minutes (30 cycles) with the final extension at 72° C. for 10 minutes. The PCR product had expected size of~1 kb. This product was extracted by equal volume of phenol/chloroform, followed by ethanol precipitation. The purified DNA fragment was directly ligated into the plasmid vector pCR2.1 (Invitrogen Corporation, San Diego, Calif.) by T4 DNA ligase (Boehringer Mannheim, Indianapolis, Ind.), and transformed into the DH5α cells (GIBCO-BRL, Grand Island, N.Y.). The clones containing monkey GnRHR were identified by restriction digests. Plasmid DNA was prepared by Qiagen kit (Qiagen Inc., Valencia, Calif.), and the monkey GnRH receptor DNA was sequenced (ACGT, Inc., Northbrook, Ill.) at both strands. Four clones that were derived from independent PCRs had identical sequences (FIG. 2).

EXAMPLE 3

Isolation of the Genomic Clones of the Monkey GnRH Receptor

To determine the authentic sequences of the monkey receptor in the primers of Human 1 and Human 3, the genomic clones that contained the monkey GnRH receptor were pulled out from a monkey genomic library (Clontech Laboratories, Inc., Palo Alto, Calif.). Approximately $10^6$ phage plaques of a monkey genomic library in Lambda EMBL3 were plated on the *E. coli* strain K803 (Clontech Laboratories, Inc., Palo Alto, Calif.). The plaques were transferred to Nitrocellulose membranes (Schleicher & Schuell, Keene, N.H.), denatured, neutralized, and screened with a 1 kb fragment containing the entire ORF of the human GnRH receptor (Kakar et al., 1992, Biochem. Biophys. Res. Commun. 189, 289–295). The membranes were incubated at 42° C. in prehybridization solution (50% formamide, 1×Denhardts, 6×SSC, 0.5% SDS, 100 µg/ml salmon sperm DNA) for 3 hours followed by overnight incubation in hybridization solution (50% formamide, 1×Denhardts, 6×SSC, 100 µg/ml salmon sperm DNA) with $1\times10^6$ cpm/ml of [$^{32}$P]-labeled probe. The probe was labeled with [$^{32}$P] dCTP using a random priming kit (Amersham, Arlington Heights, Ill.). After hybridization, membranes were first washed three times with 2×SSC, 0.1% SDS at 25° C. for 30 minutes each time, and finally washed once with 0.5×SSC, 0.1% SDS at 60° C. for 30 minutes. A single positive clone was isolated following three rounds of plaque purification.

The ORF of the human GnRH receptor spans three exons (1–3) on the genome. The exon 1 contains the translational initiator and the exon 3 contains the stop codon (Fan et al., 1994, Molecular and Cellular Endoctinology. 103, R1–R6). Given the fact that monkey is closely related to human, it was assumed that the genomic organization of the monkey GnRH receptor resembles that of the human receptor. The monkey genomic clones that contained exon 1 and exon 3 of the GnRH receptor were identified by PCR using primers in exon 1 (Monkey 1+Monkey 2) and exon 3 (Monkey 5+ HRE3-down) (SEQ ID Nos. 3–6).

Phage containing either exon 1 or exon 3 of the monkey GnRH receptor was eluted from plate plaques with 1×lambda buffer (0.1 M NaCl, 10 mM MgSO$_4$ 7H$_2$O, 35 mM Tris-HCl, PH7.5) following overnight growth of approximately $10^5$ pfu/150 mm dish. After a 10 minute centrifugation at 10,000×g to remove debris, the phage solution was treated with 1 mg/ml RNAse A and DNAse I for 30 minutes at 24° C., followed by precipitation with 20% PEG (8000)/2 M NaCl for two hours on ice, and collection by centrifugation at 10,000×g for 20 minutes. Phage DNA was isolated by incubation in 0.1% SDS, 30 mM EDTA, 50 mg/ml proteinase K for one hour at 68° C., with subsequent phenol (three times) and chloroform (twice) extraction before isopropanol precipitation overnight. The monkey GnRHR DNA inserts were individually sub-cloned from lambda EMBL3 into the plasmid vector pUC118 (GIBCO-BRL, Grand Island, N.Y.). 2 µg of phage DNA was heated to 65° C. for 10 minutes, then digested with 10 units of SalI at 37° C. for 4 hours. A fragment of 12 kb (containing exon 1) or 13 kb (containing exon 3) was subcloned into pUC118 vector (GIBCO-BRL, Grand Island, N.Y.), and sequenced by primers Monkey 2 or Monkey 6 (SEQ ID Nos. 4 or 7). Sequencing results showed that the amino acid sequence of the monkey receptor was identical with that of the human receptor at both ends (FIG. 3). But the monkey DNA sequence differs from the human sequence with one base pair at the 5' primer. The serine residue at sixth position of the receptor is encoded by TCA in monkey and TCT in human (FIG. 2). About 250 bp DNA sequence in the upstream of the translational start codon ATG was also determined from the monkey genomic clones using primers of Monkey 2 (SEQ ID No. 4).

EXAMPLE 4

The Monkey GnRH Receptor

Data searches (Genbank 88, EMBL 42, Swiss-Prot 31, PIR 40, dEST, Prosite), sequence alignments and analysis of the monkey GnRH receptor nucleotide and protein sequences were carried out using the GCG Sequence Analysis Software Package (Madison, Wis.; pileup, peptide structure and motif programs), FASTA and BLAST search programs, and PC/Gene software suite from Intelligenetics (San Francisco, Calif.; protein analysis programs).

The monkey receptor contains 328 amino acids. The monkey receptor DNA has 98% homology with that of the human GnRH receptor, and its protein has 97.6% identity and 98.8% similarity with that of the human receptor. In the monkey receptor, there are eight amino acids that differ from the human receptor (FIG. 5). As the human receptor, the monkey GnRH receptor also has the characteristic of the G-protein coupled receptors with 7 putative tramsmembrance domains. The residues for glycosylation and for disulfide bond formation are well conserved between the two primate species. As the receptor from other mammaliam species, the monkey GnRH receptor also lacks a C-terminal cytoplamic tail (FIG. 5).

EXAMPLE 5

Figure 6:
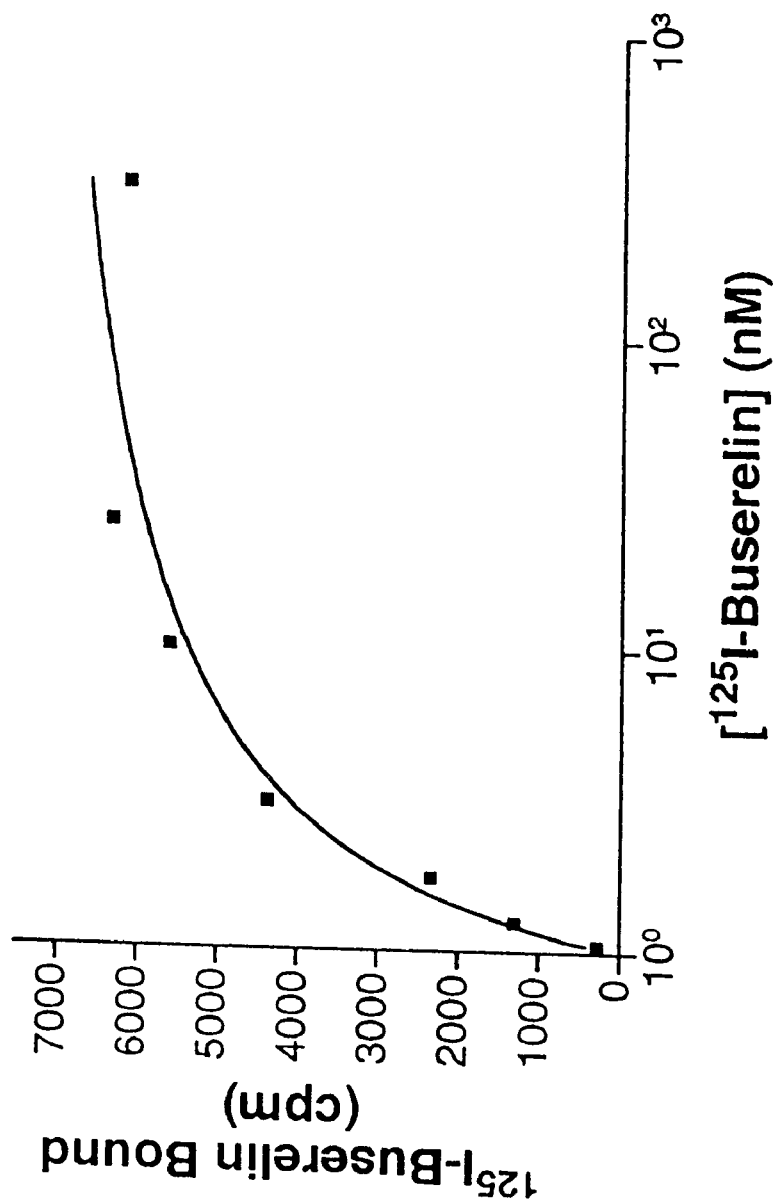
FIG. 6 is a graph demonstrating the expression of the monkey GnRH receptor in transfected CHO-K1 cells using the membrane binding assay.
Figure 7:
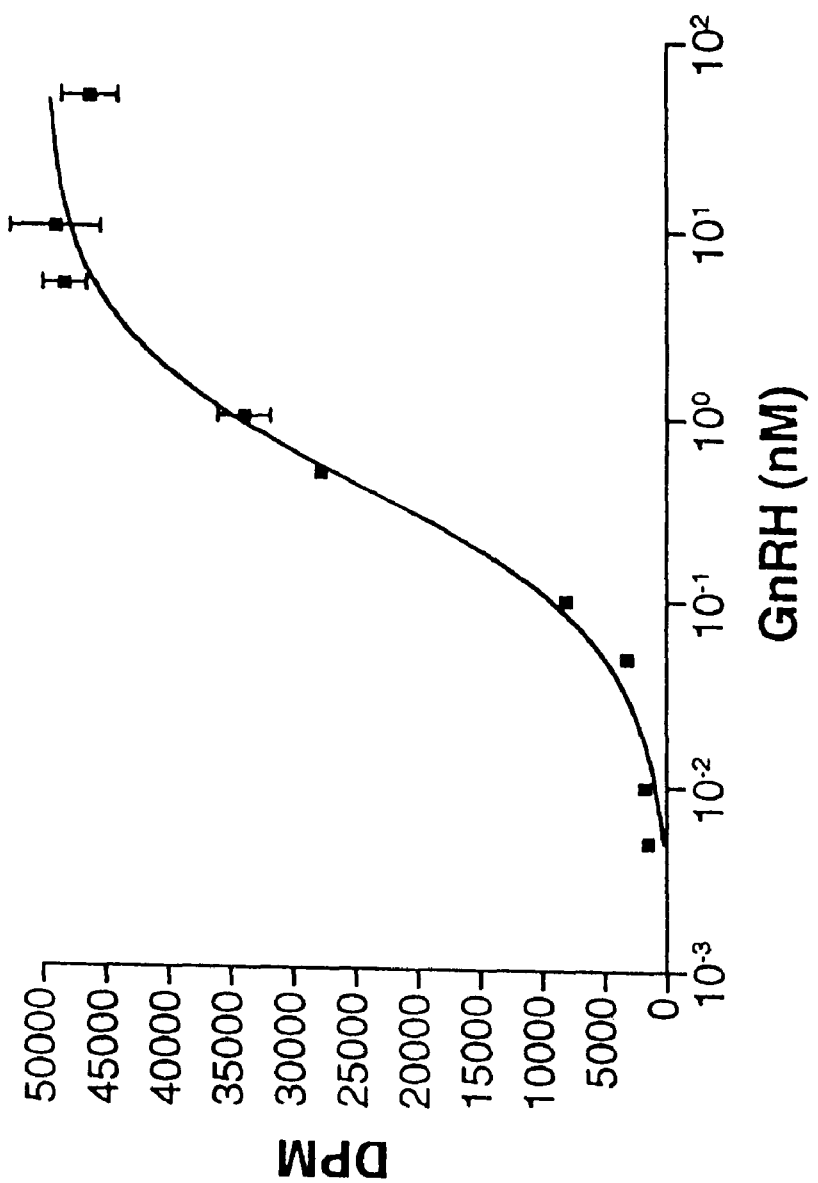
FIG. 7 is a graph demonstrating the expression of functional monkey GnRH receptor in transfected CHO-K1 cells using the PI turnover assay.
Figure 8:
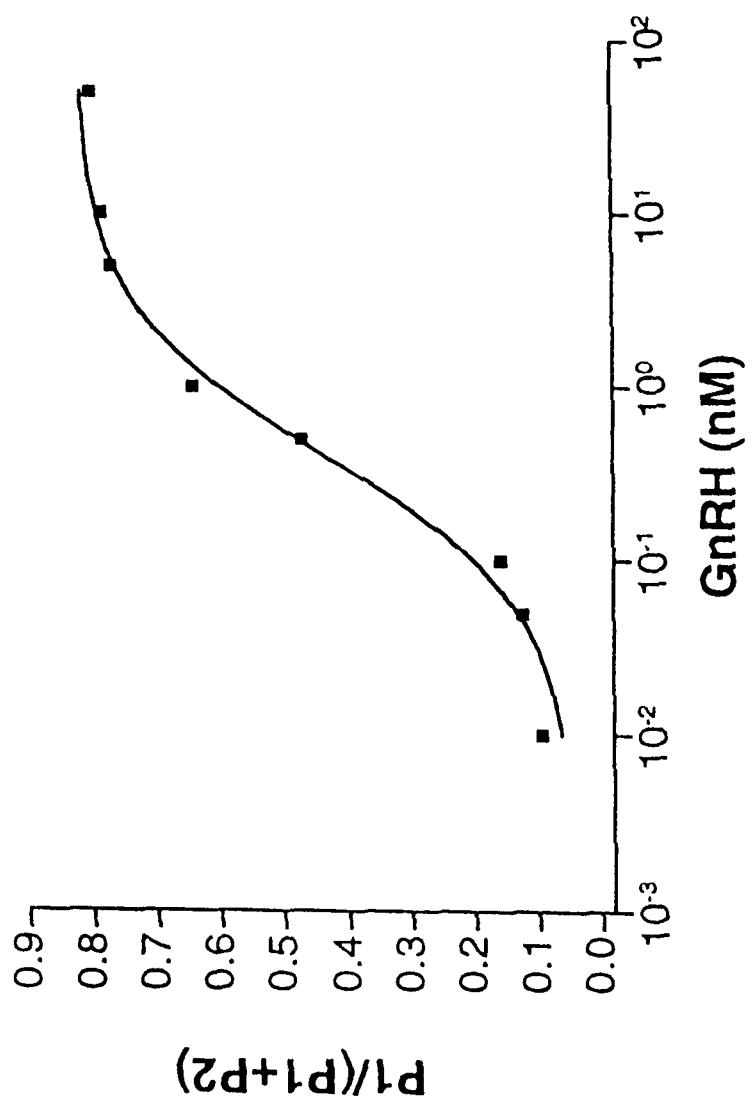
FIG. 8 is a graph showing the GnRH-stimulated functional response of the monkey GnRH receptor in CHO-K1 cells stably co-expressing recombinant monkey GnRHR and apo-aequorin using the aequorin bioluminescence assay.
Figure 9:
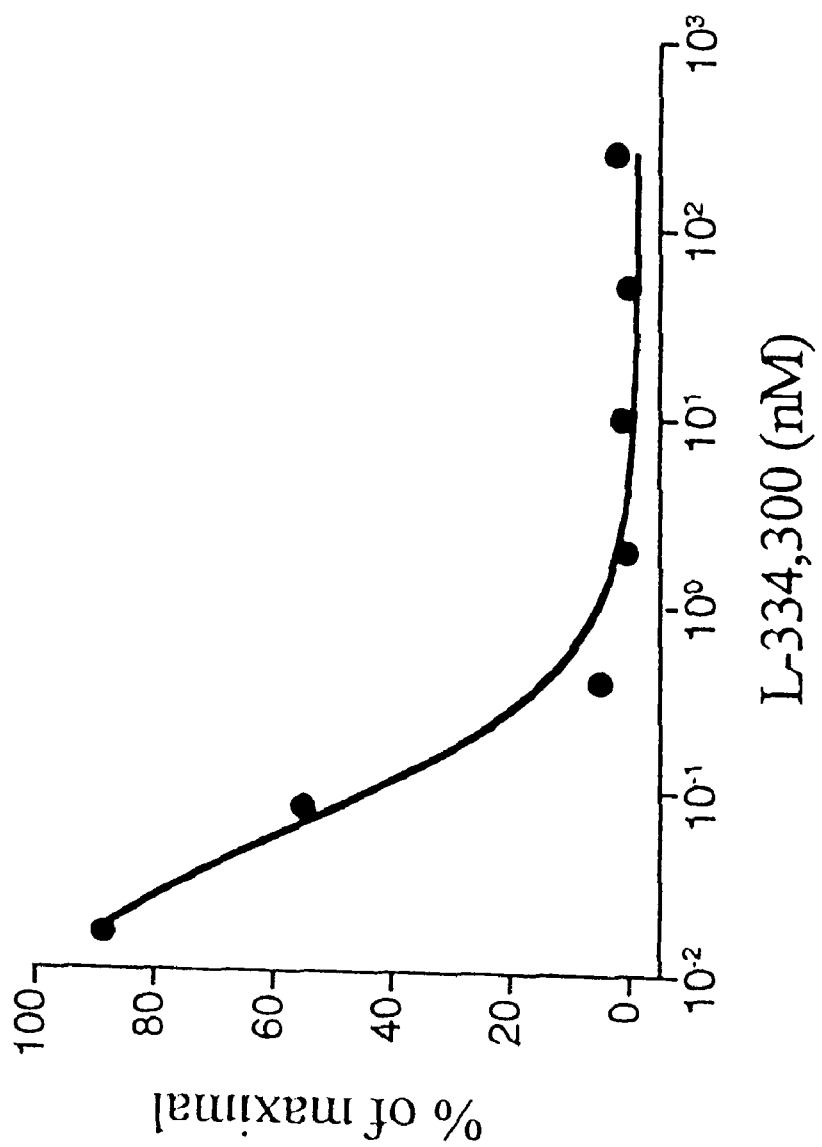
FIG. 9 is a graph showing the titration of GnRH-stimulated functional response of the monkey GnRH receptor by the antagonist Cetrorelix in CHO-K1 cells transfected with monkey GnRHR and aequorin using the aequorin bioluminescence assay.

Generation of the CHO-K1 Cells That Stably Express the Monkey GnRH Receptors The ORF of the monkey GnRH receptor was subcloned into a polycistronic expression vector pIRES1.neo (Clontech Laboratories, Palo Alto, Calif.) to generate cells that stably express these receptors. In this vector, the cloned receptor cDNA and the neo gene were transcribed into one mRNA. The plasmid DNA of pIRES1.neo-mkGnRHR was transfected into CHO-K1 cells using the method of lipofectin. Transfection was carried out for overnight and the cells were split 48 hours later. G418 at 1 mg/ml was added 24 hours after splitting, and its concentration was increased to 2 mg/ml in 2–3 days. After 10 days selection by G418, colonies were picked and transferred to 24-well plates. The monkey GnRH receptor expression clones were screened by the whole cell binding assay using a radiolabeled peptide agonist of GnRH, 5-($^{125}$Iodo-Tyr)-Buserelin (Woods Assay, Portland, Oreg.). Eight of the 96 neo$^R$ clones screened had a specific binding activity of 3-fold above the non-specific binding. The best one had a specific binding activity of 645 cpm, 5-fold above the background. After single cell isolation, the membrane from this clone was prepared, and the membrane binding assay was performed using $^{125}$I-buserelin. FIG. 6 shows that the ligand binding activity was dose-dependent. The GnRH-stimulated PI turnover was also performed. This cell line also responded to GnRH stimulation in a dose-dependent manner with an $EC_{50}$ value of 0.43 nM (FIG. 7), demonstrating that these cells are functionally well coupled with G-proteins.

EXAMPLE 6

Generation of CHO-K1 Cells That Stably Coexpress the Monkey GnRH Receptor and Apo-aeguorin To construct this dual stable cell line, the 600 bp aeq gene was cut out by EcoRI and KpnI from pcDNA3.aeq, and inserted into pIRES1hyg (Clontech Laboratories, Palo Alto, Calif.) at BamHI that was blunt-ended. The positive clones were identified by colony-hybridization using the probe of aeq. The new construct that contained aeq and hyg was transfected into monkey GnRHR-CHO-K1 cells (as Example 5). The transfectants were selected by 600 μg/ml hygromycin (Boehringer Mannheim, Indianapolis, Ind.) for 10 days, and 480 hyg$^r$ colonies were transferred into 96-well plates. These clones were assayed for aequorin by the aequorin bioluminescence assay as described in Example 7, and many positive clones were identified. The best clone had a P1/(P1+P2) ratio of 71% and an AUC of 1290 for P1. This clone was single cell isolated, and used for the functional evaluation of the monkey GnRH receptor by the aequorin assay.

EXAMPLE 7

BIOASSAYS

Membrane Binding Assay

The ligand binding assay was conducted with the monkey GnRH receptor obtained from CHO-K1 cells stably expressing the cloned receptor. Crude membrane suspensions were prepared from monkey GnRHR-CHO-K1 cells and stored as aliquots at −80° C. The radioactive peptide ligand [5-($^{125}$Iodo-Tyr)-Buserelin] was obtained from Woods Assay (Portland, Oreg.) and had a radioactive specific activity of 1000 Ci/mmol. The membranes and radioligand were diluted in assay buffer which consists of 50 mM Tris-HCl (PH 7.5), 2 mM $MgCl_2$ and 0.1% bovine serum albumin. The ligand binding assay was performed at 22° C. for 1 hour in borosilicate glass tubes in a final volume of 500 ml. Each tube contained an appropriate concentration of the radioligand (from 0.025 to 2.5 nM) and 15–20 mg of monkey GnRH receptor membrane protein. The incubation was terminated by vacuum filtration onto GF/C Whatman filter paper (pretreated with 0.1% BSA in PBS) by a Brandel 48-well Harvester and then washed with 2 ml of cold phosphate saline (PH 7.5). The filter strips were counted in a Gamma Counter.

Phosphoinositide (PI) Turnover Assay

CHO-K1 cells stably expressing the monkey GnRH receptor are functionally coupled to phospholipase C. To perform the PI turnover assay, the monkey GnRHR-CHO-K1 cells were seeded into 24-well plates at a concentration of 80,000 cells/ml/well in inositol-free F12 medium (Gibco Life Technology, Grand Island, N.Y.) containing 10% dialyzed fetal bovine serum (Gibco Life Technology, Grand Island, N.Y.), 1% Pen/Strep, 2 mM glutamine, 2 mg/ml G418 and 1 μCi ($^3$H) inositol (NEN Life Sciences, Boston, Mass.). Forty-eight hours after seeding, cells were washed with 3×1 ml of PBS containing 10 mM LiCl and treated with various concentrations of GnRH (Biochem, Torrance, Calif.). After incubation at 37° C. for 1 hour, the medium was removed and the cells were lysed with 1 ml of 0.1 M formic acid. The plates were freeze-thawed once and the cell extract was applied onto a Dowex AG1-X8 column (Bio-Rad Labs, Hercules, Calif.). The column was washed with 2×1 ml $H_2O$ to remove free ($^3$H)inositol, and ($^3$H)inositol phosphates were eluted with 3×1 ml 2 M ammonium formate in 1 M formic acid. The eluate was then counted in a scintillation counter.

Aequorin Bioluminescence Assay

The aequorin assay has been widely used to monitor the changes in the cytosolic $Ca^{2+}$ concentration caused by the activation of the G-protein coupled receptors. The aequorin assay was conducted with the monkey GnRH receptor in CHO-K1 cells stably co-expressing the monkey GnRH receptor and apo-aequorin. These cells were maintained in the F12 medium (Gibco Life Technology, Grand Island, N.Y.). On the day of the experiment, cells were first charged with 10 μM coelenterazine (Molecular Probes, Inc., Eugene, Oreg.) in DMEM medium (Gibco Life Technology, Grand Island, N.Y.) for 2 hours at 37° C. The charged cells were washed and suspended in ECB buffer which consists of 140 mM NaCl, 20 mM KCl, 20 mM HEPES (PH 7), 5 mM glucose, 1 mM MgCl2, 1 mM $CaCl_2$, and 0.01% BSA (fatty acid free, Sigma, St. Louis, Mo.) and dispensed into wells of a 96-well plate (Pachard Instrument Company Inc., One State Street, CT) containing various concentrations of GnRH. The plate was read immediately in a Bioluminomitor (Lumino Skan RS) for 30 seconds. The first response (area under the curve) was designated as P1. The remaining unreacted aequorin was determined by lysing the cells with 0.1% Triton X-100 (Sigma, St. Louis, Mo.). The second response was designated as P2. The percentage of aequorin which responded to GnRH challenge was calculated as P1/(P1+P2).

To assay the antagonist Cetrorelix (Woods Assay, Portland, Oreg.), the charged cells were aliquoted into a 96-well plate and incubated with various concentrations of Cetrorelix at 37° C. for 30 min. After incubation, GnRH was added to each well to achieve a final concentration of 2 nM (the $EC_{50}$ value), and the plate was read similarly as for GnRH. This value of P1/(P1+P2) in the absence of Cetrorelix represents the maximal effect of GnRH (100%). The inhibitory effect of Cetrorelix was expressed relatively to this value.

What is claimed is:

1. A purified DNA molecule encoding a monkey gonadotropin releasing hormone (GnRH) receptor which comprises the nucleotide sequence, SEQ ID No. 8.

2. A purified DNA molecule encoding a monkey gonadotropin releasing hormone (GnRH) receptor wherein said DNA molecule encodes a protein comprising the amino acid sequence, SEQ ID No. 9.

3. An expression vector for the expression of the monkey GnRH receptor in a recombinant host cell wherein said expression vector comprises a DNA molecule which encodes the amino acid sequence of claim 2.

4. The expression vector according to claim 3 which is selected from the group consisting of plasmids, modified viruses, yeast artificial chromosomes, bacteriophages, cosmids and transposable elements.

5. A host cell which expresses a recombinant monkey GnRH receptor wherein said host cell contains the expression vector of claim 3.

6. A host cell which expresses a recombinant monkey GnRH receptor wherein said host cell contains the expression vector of claim 4.

* * * * *

SEQUENCE LISTING

<160> NUMBER OF SEQ ID NOS: 10

<210> SEQ ID NO 1
<211> LENGTH: 36
<212> TYPE: DNA
<213> ORGANISM: Artificial Sequence
<220> FEATURE:
<223> OTHER INFORMATION: Artificial Primer

<400> SEQUENCE: 1
atgcgaattc gccaccatgg caaacagtgc ctctcc       36

<210> SEQ ID NO 2
<211> LENGTH: 40
<212> TYPE: DNA
<213> ORGANISM: Artificial Sequence
<220> FEATURE:
<223> OTHER INFORMATION: Artificial Primer
<220> FEATURE:
<221> NAME/KEY: misc_feature
<222> LOCATION: (1)...(40)
<223> OTHER INFORMATION: n=A, C, T or G

<400> SEQUENCE: 2
atgctctaga tcacagagaa aaatatccat agataagtgg       40

<210> SEQ ID NO 3
<211> LENGTH: 19
<212> TYPE: DNA
<213> ORGANISM: Artificial Sequence
<220> FEATURE:
<223> OTHER INFORMATION: Artificial Primer
<220> FEATURE:
<221> NAME/KEY: misc_feature
<222> LOCATION: (1)...(19)
<223> OTHER INFORMATION: n=A, C, T or G

<400> SEQUENCE: 3
acttcagaag tggacacag       19

<210> SEQ ID NO 4
<211> LENGTH: 21
<212> TYPE: DNA
<213> ORGANISM: Artificial Sequence
<220> FEATURE:
<223> OTHER INFORMATION: Artificial Primer
<220> FEATURE:
<221> NAME/KEY: misc_feature
<222> LOCATION: (1)...(21)
<223> OTHER INFORMATION: n=A, C, T or G

<400> SEQUENCE: 4
cagaggaact ctccagcata c       21

<210> SEQ ID NO 5
<211> LENGTH: 21
<212> TYPE: DNA
<213> ORGANISM: Artificial Sequence
<220> FEATURE:
<223> OTHER INFORMATION: Artificial Primer
<220> FEATURE:
<221> NAME/KEY: misc_feature
<222> LOCATION: (1)...(21)
<223> OTHER INFORMATION: n=A, C, T or G

<400> SEQUENCE: 5
atatccatag ataagtggat c       21

<210> SEQ ID NO 6
<211> LENGTH: 23
<212> TYPE: DNA
<213> ORGANISM: Artificial Sequence
<220> FEATURE:
<223> OTHER INFORMATION: Artificial Primer
<220> FEATURE:
<221> NAME/KEY: misc_feature
<222> LOCATION: (1)...(23)
<223> OTHER INFORMATION: n=A, C, T or G

<400> SEQUENCE: 6
tccatagata agtggatcaa agc                                            23

<210> SEQ ID NO 7
<211> LENGTH: 19
<212> TYPE: DNA
<213> ORGANISM: Artificial Sequence
<220> FEATURE:
<223> OTHER INFORMATION: Artificial Primer
<220> FEATURE:
<221> NAME/KEY: misc_feature
<222> LOCATION: (1)...(19)
<223> OTHER INFORMATION: n=A, C, T or G

<400> SEQUENCE: 7
cattcactgt ctgctggac                                                 19

<210> SEQ ID NO 8
<211> LENGTH: 986
<212> TYPE: DNA
<213> ORGANISM: Macacca mulatta

<400> SEQUENCE: 8
atggcaaaca gtgcctcacc tgaacagaat caaaatactg ttcagtcatc aacaacagca    60
tcccactgat gcagggcaac ctccccactc tgaccttgtc tggaaagatc cgagtgacag   120
ttactttctt ccttttttcta ctctctgcga cctttaatgc ttctttcctg ctgaaacttc   180
agaagtggac acagaagaaa gagaagggaa aaagctgtc aagaatgaag ctgctcttaa    240
aacatctgac cttagccaac ctgttggaga ctctgattgt catgccactg gatgggatgt   300
ggaacattac agtccaatgg tatgctggag agttcctctg caaagttctc agttatctaa   360
agcttttctc catgtatgcc ccagctttca tgatggtggt gatcagcctg accgctccc    420 tggctatcac gaggccccta gctttgaaaa gcagcagcaa gctcggacag tccatggttg   480
gcctggcctg gatcctcagt agtgtctttg caggaccaca gttatacatc ttcaggatga   540
ttcatctagc agacagctcc ggacagacaa agttttctc tcaatgtgta acacactgca   600
gttttccaca atggtggcat caagcatttt ataactttt caccttcagc tgcctcttca   660
tcatccctct tctcatcatg ctgatctgca atgcaaaaat catcttcacc ctgacacggg   720
tccttcatca ggatccccac aaactacaac tgaatcagtc caagaacaat ataccaagag   780
cacggctgaa gactctaaaa atgacagttg catttgccac ttcattcact gtctgctgga   840
ctccctacta tgtcctagga atttggtatt ggtttgatcc tgaaatgtta aacagggtgt   900
cagacccagt aaatcacttc ttctttctct ttgcctttt aaacccatgc tttgatccac   960
ttatctatgg atattttct ctgtga                                         986

<210> SEQ ID NO 9
<211> LENGTH: 328
<212> TYPE: PRT

<210> ORGANISM: Macaca mulatta

<400> SEQUENCE: 9

| | | | | | | | | | | | | | | |
|---|---|---|---|---|---|---|---|---|---|---|---|---|---|---|
| Met | Ala | Asn | Ser | Ala | Ser | Pro | Glu | Gln | Asn | Gln | Asn | His | Cys | Ser | Val |
| 1 | | | | 5 | | | | | 10 | | | | | 15 | |
| Ile | Asn | Asn | Ser | Ile | Pro | Leu | Met | Gln | Gly | Asn | Leu | Pro | Thr | Leu | Thr |
| | | | | 20 | | | | | 25 | | | | | 30 | |
| Leu | Ser | Gly | Lys | Ile | Arg | Val | Thr | Val | Thr | Phe | Phe | Leu | Phe | Leu | Leu |
| | | | | 35 | | | | | 40 | | | | | 45 | |
| Ser | Ala | Thr | Phe | Asn | Ala | Ser | Phe | Leu | Leu | Lys | Leu | Gln | Lys | Trp | Thr |
| | | | | 50 | | | | | 55 | | | | | 60 | |
| Gln | Lys | Lys | Glu | Lys | Gly | Lys | Lys | Leu | Ser | Arg | Met | Lys | Leu | Leu | Leu |
| 65 | | | | | 70 | | | | | 75 | | | | | 80 |
| Lys | His | Leu | Thr | Leu | Ala | Asn | Leu | Leu | Glu | Thr | Leu | Ile | Val | Met | Pro |
| | | | | 85 | | | | | 90 | | | | | 95 | |
| Leu | Asp | Gly | Met | Trp | Asn | Ile | Thr | Val | Gln | Trp | Tyr | Ala | Gly | Glu | Phe |
| | | | | 100 | | | | | 105 | | | | | 110 | |
| Leu | Cys | Lys | Val | Leu | Ser | Tyr | Leu | Lys | Leu | Phe | Ser | Met | Tyr | Ala | Pro |
| | | | | 115 | | | | | 120 | | | | | 125 | |
| Ala | Phe | Met | Met | Val | Val | Ile | Ser | Leu | Asp | Arg | Ser | Leu | Ala | Ile | Thr |
| | | | | 130 | | | | | 135 | | | | | 140 | |
| Arg | Pro | Leu | Ala | Leu | Lys | Ser | Ser | Lys | Leu | Gly | Gln | Ser | Met | Val |
| 145 | | | | | 150 | | | | | 155 | | | | | 160 |
| Gly | Leu | Ala | Trp | Ile | Leu | Ser | Ser | Val | Phe | Ala | Gly | Pro | Gln | Leu | Tyr |
| | | | | 165 | | | | | 170 | | | | | 175 | |
| Ile | Phe | Arg | Met | Ile | His | Leu | Ala | Asp | Ser | Ser | Gly | Gln | Thr | Lys | Val |
| | | | | 180 | | | | | 185 | | | | | 190 | |
| Phe | Ser | Gln | Cys | Val | Thr | His | Cys | Ser | Phe | Pro | Gln | Trp | Trp | His | Gln |
| | | | | 195 | | | | | 200 | | | | | 205 | |
| Ala | Phe | Tyr | Asn | Phe | Phe | Thr | Phe | Ser | Cys | Leu | Phe | Ile | Ile | Pro | Leu |
| | | | | 210 | | | | | 215 | | | | | 220 | |
| Leu | Ile | Met | Leu | Ile | Cys | Asn | Ala | Lys | Ile | Ile | Phe | Thr | Leu | Thr | Arg |
| 225 | | | | | 230 | | | | | 235 | | | | | 240 |
| Val | Leu | His | Gln | Asp | Pro | His | Lys | Leu | Gln | Leu | Asn | Gln | Ser | Lys | Asn |
| | | | | 245 | | | | | 250 | | | | | 255 | |
| Asn | Ile | Pro | Arg | Ala | Arg | Leu | Lys | Thr | Leu | Lys | Met | Thr | Val | Ala | Phe |
| | | | | 260 | | | | | 265 | | | | | 270 | |
| Ala | Thr | Ser | Phe | Thr | Val | Cys | Trp | Thr | Pro | Tyr | Tyr | Val | Leu | Gly | Ile |
| | | | | 275 | | | | | 280 | | | | | 285 | |
| Trp | Tyr | Trp | Phe | Asp | Pro | Glu | Met | Leu | Asn | Arg | Val | Ser | Asp | Pro | Val |
| | | | | 290 | | | | | 295 | | | | | 300 | |
| Asn | His | Phe | Phe | Phe | Leu | Phe | Ala | Phe | Leu | Asn | Pro | Cys | Phe | Asp | Pro |
| 305 | | | | | 310 | | | | | 315 | | | | | 320 |
| Leu | Ile | Tyr | Gly | Tyr | Phe | Ser | Leu |
| | | | | 325 | | | |

<210> SEQ ID NO 10
<211> LENGTH: 244
<212> TYPE: DNA
<213> ORGANISM: Macaca mulatta

<400> SEQUENCE: 10
acatgtggcc ctcagaatgc gtttggcctg ctctgtttta gccctctgtt ggattaccaa    60
tacacaaaac aagttaacct tgatctttct cattaagtat ctcagggaca aaatttgaca   120

-continued

```
tacgtctaaa cctgtgacgt ttccatctaa agaaggcaga aataaaacag gactttagat      180
tcggttacaa taaaatatca gatgcgccac agacacaagt cttgaagctc tgtcctggga      240
aaat                                                                   244
```